United States Patent
Shuler et al.

(10) Patent No.: US 11,406,527 B2
(45) Date of Patent: Aug. 9, 2022

(54) AIRFLOW INHIBITOR APPARATUS

(71) Applicant: OptiO2 Labs LLC, Albertville, AL (US)

(72) Inventors: Jacob Thomas Shuler, Nolensville, TN (US); Joseph Austin Mallette, Nashville, TN (US)

(73) Assignee: OptiO2 Labs LLC, Albertville, AL (US)

( * ) Notice: Subject to any disclaimer, the term of this patent is extended or adjusted under 35 U.S.C. 154(b) by 10 days.

(21) Appl. No.: 16/920,669

(22) Filed: Jul. 4, 2020

(65) Prior Publication Data

US 2021/0000639 A1 Jan. 7, 2021

Related U.S. Application Data

(60) Provisional application No. 62/870,947, filed on Jul. 5, 2019.

(51) Int. Cl.
*A61F 5/56* (2006.01)
*A63B 23/18* (2006.01)

(52) U.S. Cl.
CPC .............. *A61F 5/566* (2013.01); *A63B 23/18* (2013.01)

(58) Field of Classification Search
CPC ...... A61F 5/566; A61F 5/56; A61F 2005/563; A61F 5/58; A61F 5/0003; A61F 5/0006; A61C 7/08; A61C 17/10; A61C 5/90; A63B 71/085; A63B 2071/086; A63B 2071/088; A63B 23/032
USPC .......................................... 128/848; 433/140
See application file for complete search history.

(56) References Cited

U.S. PATENT DOCUMENTS

| | | | |
|---|---|---|---|
| 2,521,039 A * | 9/1950 | Carpenter | A63B 71/085 128/861 |
| 2,521,084 A * | 9/1950 | Oberto | A61M 16/10 128/206.29 |
| 3,496,936 A * | 2/1970 | Gores | A63B 71/085 128/861 |
| 6,152,138 A | 11/2000 | Brown | |
| 10,245,397 B2 | 4/2019 | Kashefi-Khorasani et al. | |
| 2011/0212811 A1 | 9/2011 | Rutten | |
| 2017/0165102 A1* | 6/2017 | Walls | A61F 5/566 |
| 2018/0028297 A1* | 2/2018 | Lin | A61F 5/566 |

(Continued)

FOREIGN PATENT DOCUMENTS

| | | |
|---|---|---|
| EP | 0 720 493 B1 | 6/1999 |
| JP | 3068058 U | 4/2000 |

*Primary Examiner* — Victoria Hicks Fisher
(74) *Attorney, Agent, or Firm* — Aslan Law, P.C.

(57) ABSTRACT

An airflow inhibitor apparatus for use in the mouth has an airflow inhibitor body and a tongue shelf. The tongue shelf positions the forward part of the tongue upward, improving the oral posture of the wearer and promoting proper nasal breathing. The airflow inhibitor body helps block the user from mouth breathing. The body is adjacent to the lips and the teeth when in the mouth. The tongue shelf extends laterally from the body. A bite pad may be shaped to fit the teeth of the wearer, having been made with reference to a custom mold or the like, or may have a combination of protrusions that permit the teeth to grip the pad. In an alternative configuration, the body has thinned wall sections that facilitate trimming of the airflow inhibitor apparatus with scissors or the like.

12 Claims, 14 Drawing Sheets

(56) References Cited

U.S. PATENT DOCUMENTS

2018/0344507 A1\* 12/2018 Alglave ................ A61F 5/566
2019/0021820 A1\* 1/2019 Lucera .................. A61F 5/566

\* cited by examiner

AIRFLOW INHIBITOR APPARATUS

CROSS-REFERENCE TO RELATED APPLICATIONS

This application claims priority from and is a non-provisional application of U.S. Provisional Patent Application 62/870,947 filed on Jul. 5, 2019, the entirety of which is incorporated herein by this reference.

FIELD

The discussion below relates to an airflow inhibitor apparatus intended for use in a human mouth to inhibit mouth breathing and promote nasal breathing.

SUMMARY

As described more fully below, an airflow inhibitor apparatus in one example may restrict airflow via the mouth or oral cavity, encouraging the wearer to breathe through the nose when exercising, training, sleeping, resting, or other activities.

One general aspect includes an airflow inhibitor apparatus. The airflow inhibitor apparatus includes an airflow inhibitor body, adapted to be disposed in the human mouth between the lips and the teeth; the airflow inhibitor body having a body outer surface and a body inner surface, the body outer surface being adjacent to the lips and the body inner surface being adjacent to the teeth when disposed in the human mouth; the airflow inhibitor body having a body wall between the body outer surface and the body inner surface; the body wall having a body upper edge and a body lower edge, the body upper edge being nearer to the upper jaw and the body lower edge being nearer to the lower jaw when disposed in the human mouth; the airflow inhibitor body having a first recess centrally disposed along the body upper edge; the airflow inhibitor body having a second recess centrally disposed along the body lower edge; a tongue shelf attached to the body inner surface of the airflow inhibitor body; the tongue shelf extending laterally from and centered upon the body inner surface; the tongue shelf having a shelf upper surface and a shelf lower surface, the shelf upper surface being nearer the upper jaw and the shelf lower surface being nearer the lower jaw when disposed in the human mouth; the tongue shelf having a shelf wall between the shelf upper surface and the shelf lower surface; the tongue shelf having a shelf rearward edge, the shelf rearward edge being nearer to the tongue than to the teeth when disposed in the human mouth; and the tongue shelf having a tongue recess centrally disposed along the shelf rearward edge.

In another general aspect, the airflow inhibitor apparatus includes an airflow inhibitor body, the airflow inhibitor body being an arcuate, being curved symmetrically about a first axis, extending horizontally along a second axis, and extending depthwise along a third axis; the airflow inhibitor body having: a body outer surface that is convex and a body inner surface that is concave, the body outer surface defining a forward direction of the third axis and the body inner surface defining a rearward direction of the third axis; a body wall between the body outer surface and the body inner surface, the body wall having a body upper edge in an upward direction of the first axis and a body lower edge in a downward direction of the first axis; a line of symmetry along a plane that contains the first axis and the third axis; a first recess disposed along the line of symmetry along the body upper edge; and a second recess disposed along the line of symmetry along the body lower edge. The apparatus also includes a tongue shelf, attached to the body inner surface and extending in the rearward direction, the tongue shelf having: a shelf upper surface in the upward direction and a shelf lower surface in the downward direction, a shelf wall between the shelf upper surface and the shelf lower surface, a shelf rearward edge in the rearward direction, and a tongue recess along the shelf rearward edge.

BRIEF DESCRIPTION OF THE DRAWING FIGURES

DETAILED DESCRIPTION

Figure 1:
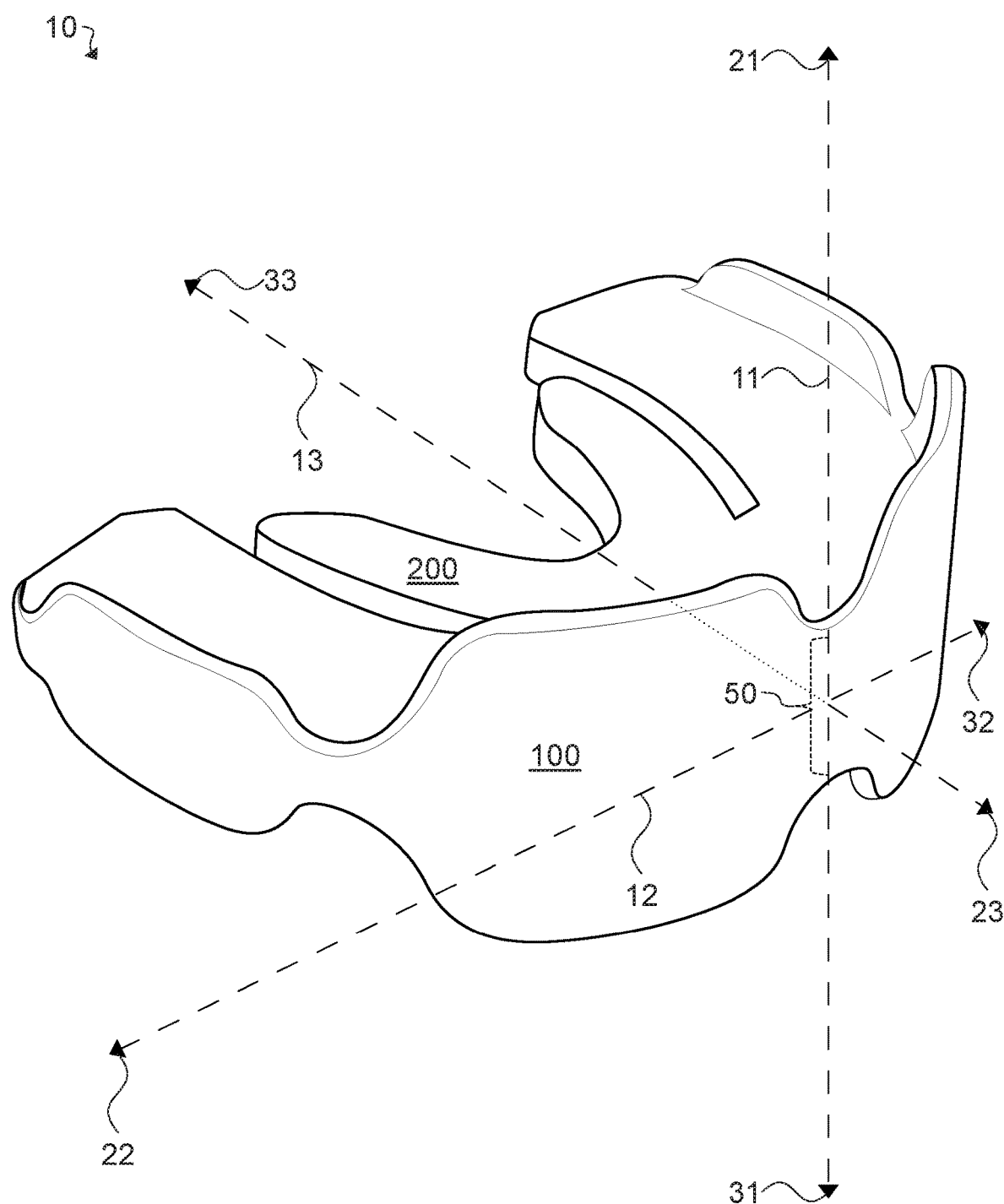
FIG. 1 shows an oblique, perspective view of an airflow inhibitor apparatus and a three-dimensional coordinate system.

Referring to FIG. 1, there is shown an airflow inhibitor apparatus 10. In FIG. 1, the airflow inhibitor apparatus 10 has two principle parts, an airflow inhibitor body 100 and a tongue shelf 200.

The airflow inhibitor body 100 inhibits the flow of air into and from the mouth. The airflow inhibitor body 100 may completely block such airflow. The airflow inhibitor body 100 has a somewhat flat shape that symmetrically curves about an axis parallel to a vertical axis 11 and generally into an arcuate, with various adaptations to suit the anatomy of the human mouth so it can comfortably be disposed between the lips and the teeth, fit between the upper jaw and the lower jaw, and accommodate the tongue.

Since the airflow inhibitor body 100 curves symmetrically about an axis parallel to a vertical axis 11, the airflow inhibitor body 100 may be understood to have a central vertical line of symmetry 50 that may generally define two halves of the airflow inhibitor body 100: a right half and a left half. The halves of the airflow inhibitor body 100 extend leftward 22 or rightward 32 in a way that may be understood to define a horizontal axis 12.

Figure 2:
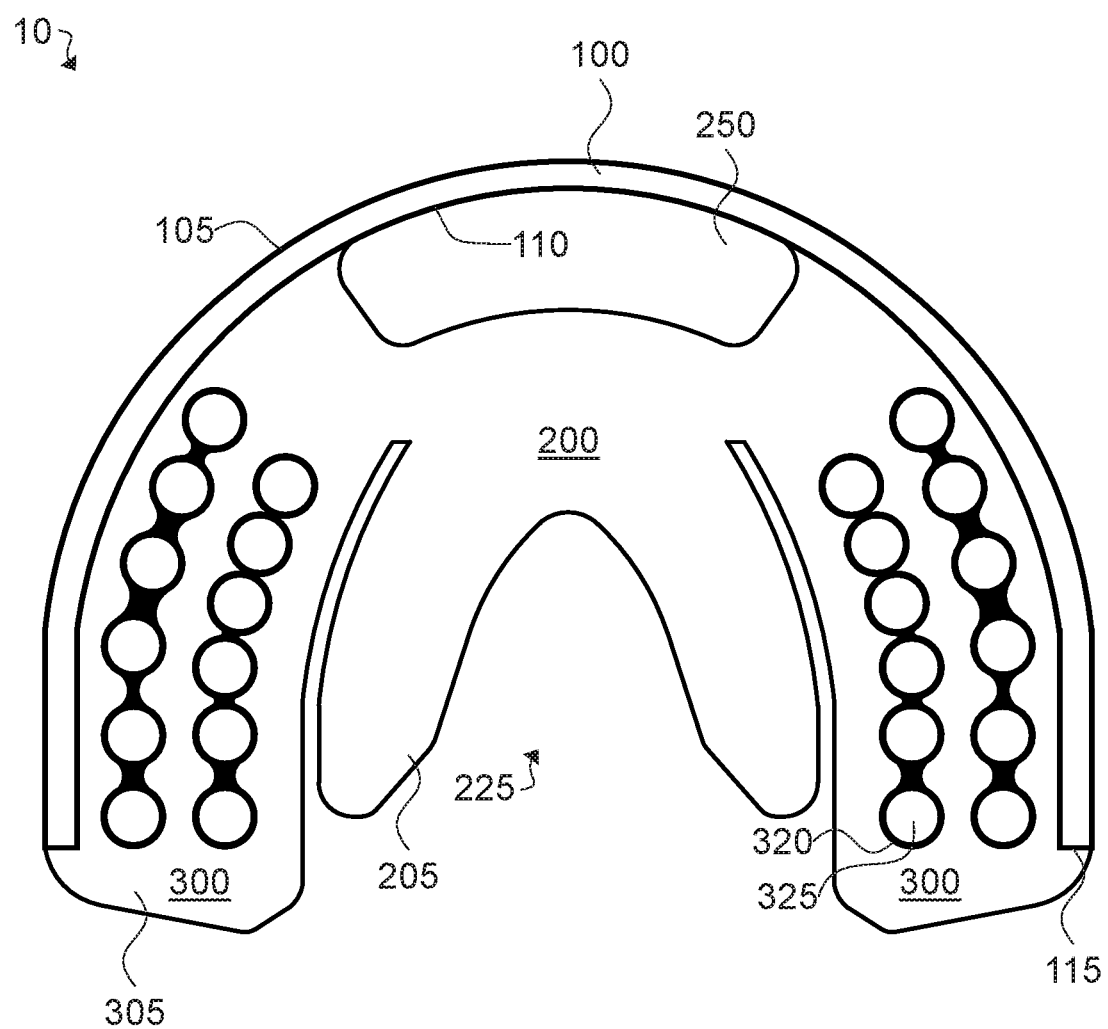
FIG. 2 shows the airflow inhibitor apparatus viewed from the top.

Referring now also to FIG. 2, The airflow inhibitor body 100 has a body outer surface 105 and a body inner surface 110. The body outer surface 105 is the surface of the airflow inhibitor body 100 that is on the outer, convex side of the arcuate, and the body inner surface 110 is the surface of the airflow inhibitor body 100 that is on the inner, concave side of the arcuate. When disposed in the mouth, the body outer surface 105 is toward the lips and the body inner surface 110 is toward the teeth. This does not imply that the body outer surface 105 must touch the lips or that the body inner surface 110 must touch the teeth.

At the central, vertical line of symmetry 50 of the airflow inhibitor body 100, and along a plane that also intersects the horizontal axis 12, the body outer surface 105 may be understood to define a front aspect of the airflow inhibitor apparatus 10, and the body inner surface 110 may at that location define a rear or back aspect. An axis passing through the intersection of the vertical axis 11 and the horizontal axis 12, and through the front and rear aspects of the airflow inhibitor body 100 may be understood to define a depthwise axis 13 with a forward direction 23 and rearward direction 33.

The vertical axis 11 may be referred to as a first axis that has the upward direction 21 and the downward direction 31. The horizontal axis 12 may be referred to as a second axis that has the left direction 22 and the right direction 32. The depthwise axis 13 may be referred to as a third axis that has the forward direction 23 and the rearward direction 33. The line of symmetry 50 may be said to be along a plane that contains the first axis and the third axis. It is not necessary that the line of symmetry coincide with the vertical axis 11.

The airflow inhibitor body 100 is an arcuate that is curved symmetrically about a first axis that is parallel to or that is the vertical axis 11. The airflow inhibitor body 100 extends horizontally along a second axis, such as the horizontal axis 12, and extends depthwise along a third axis such as the depthwise axis 13.

Figure 4:
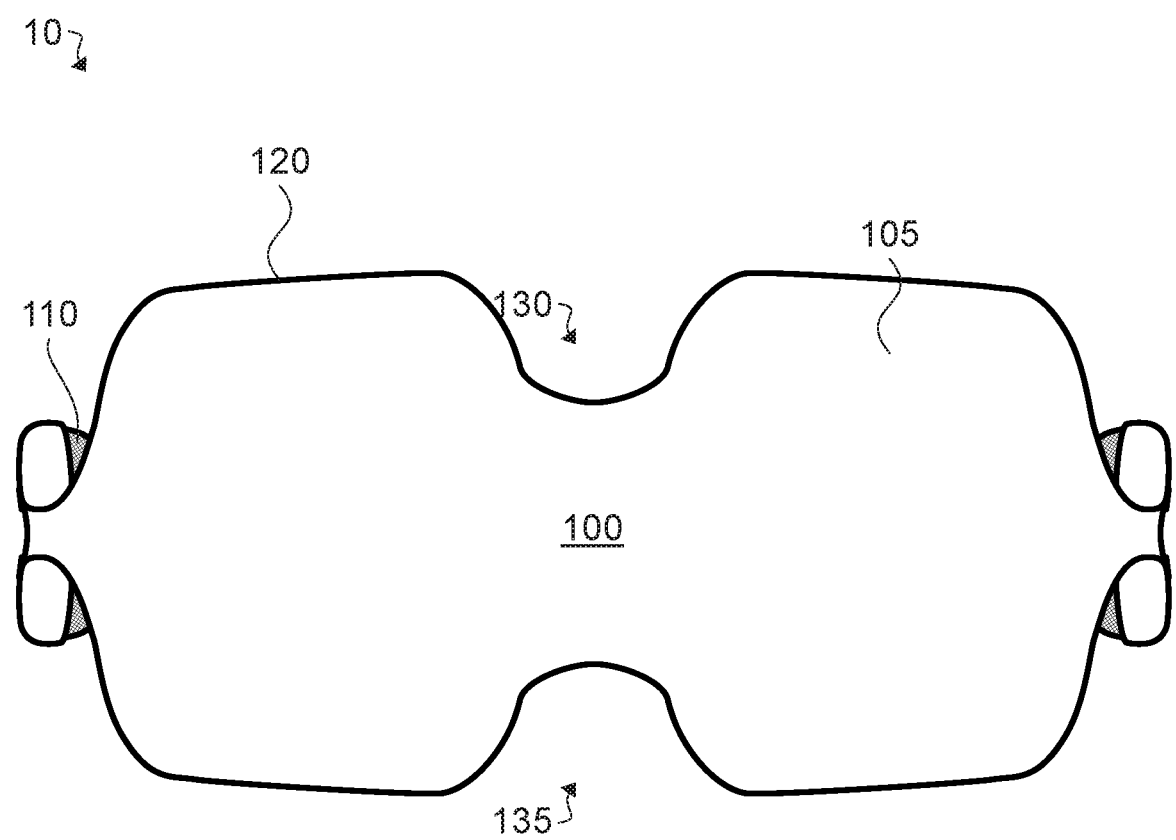
FIG. 4 shows the airflow inhibitor apparatus viewed from the front.
Figure 5:
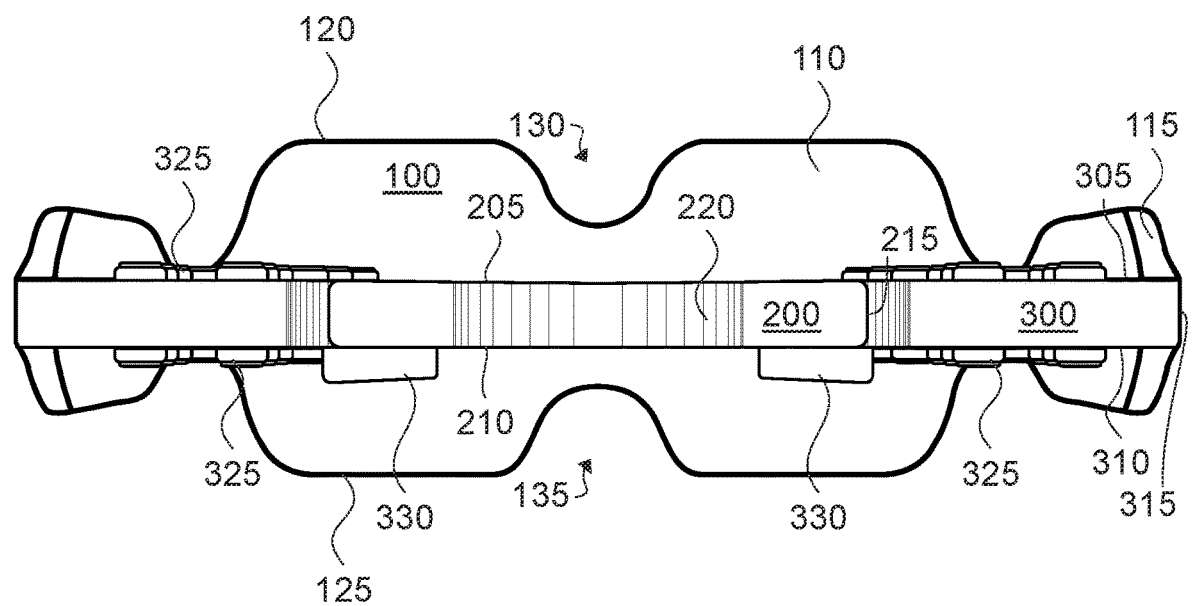
FIG. 5 shows the airflow inhibitor apparatus viewed from the rear.

FIG. 2 shows that, between the body outer surface 105 and the body inner surface 110 is a body wall 115. The body wall 115 may have a generally uniform thickness or have a thickness that varies. The body wall 115 has a body upper edge 120 in the upward direction 21 and a body lower edge 125 in the downward direction 31. FIG. 4 shows the body upper edge 120 and FIG. 5 shows the body lower edge 125. The edges may be rounded over, as shown in FIG. 1.

The body upper edge 120 may have a first recess 130, as shown in FIG. 4, that is adapted to accommodate the superior labial frenum found in the mouth. As such, the first recess 130 is disposed along the line of symmetry 50.

The body lower edge 125 may have a second recess 135 that is adapted to accommodate the inferior labial frenum. The second recess 135 is likewise disposed along the line of symmetry 50.

Figure 3:
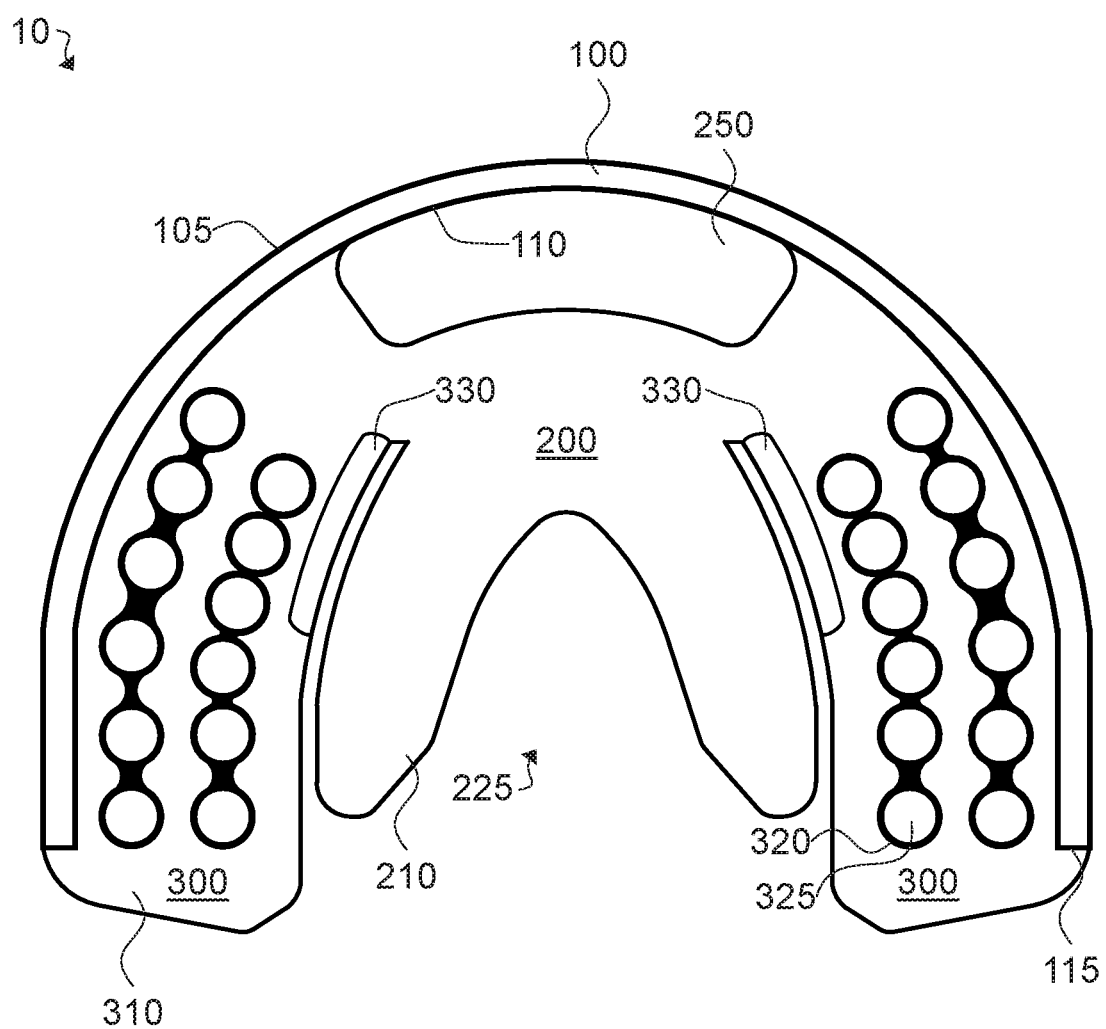
FIG. 3 shows the airflow inhibitor apparatus viewed from the bottom.

As shown in FIG. 1, and in a slightly different way in FIG. 2 and FIG. 3, the tongue shelf 200 is attached to the bite pad and extends laterally from bite pad 300 in the rearward direction 33. The tongue shelf 200 has a shelf upper surface 205 in the upward direction 21, as shown in FIG. 2, and a shelf lower surface 210 in the downward direction 31, as shown in FIG. 3. Between these two surfaces the tongue shelf 200 has a shelf wall 215. The tongue shelf 200 has a shelf rearward edge 220 as shown in FIG. 5 and a shelf forward edge spaced from the body inner surface by a hole in the bite pad. The shelf wall 215 may be rounded over to promote comfort when the airflow inhibitor apparatus 10 is in the mouth.

Along the shelf rearward edge 220 of the tongue shelf 200 is a tongue recess 225. The tongue recess 225 accommodates the area where the tongue attaches to the mouth and/or part of the tongue. The tongue fits into the tongue recess 225 and on top of the shelf upper surface 205 and thereby achieves an elevated tongue position which promotes a fully open airway.

The airflow inhibitor apparatus may be made of plastic, rubber, or other flexible material which is safe to be worn inside the mouth and not uncomfortable to the wearer. Different areas of the airflow inhibitor apparatus 10 may be made from different types of material with more or less resilience. For example, the tongue shelf 200 may be made of a more flexible material than the airflow inhibitor body 100 so that the tongue shelf 200 easily flexes upward or downward.

Returning to FIG. 2 and FIG. 3 there is shown a bite pad 300. The airflow inhibitor apparatus 10 may have a bite pad 300 that allows the user to bite thereon so that the airflow inhibitor apparatus 10 may be securely held in the mouth. The bite pad 300 may extend from the body inner surface 110 in the rearward direction 33. The bite pad 300 has a pad upper surface 305 in the upward direction 21 and a pad lower surface 310 in the downward direction 31. Between the pad upper surface 305 and the pad lower surface 310 is a pad wall 315 as shown in FIG. 5.

Figure 8:
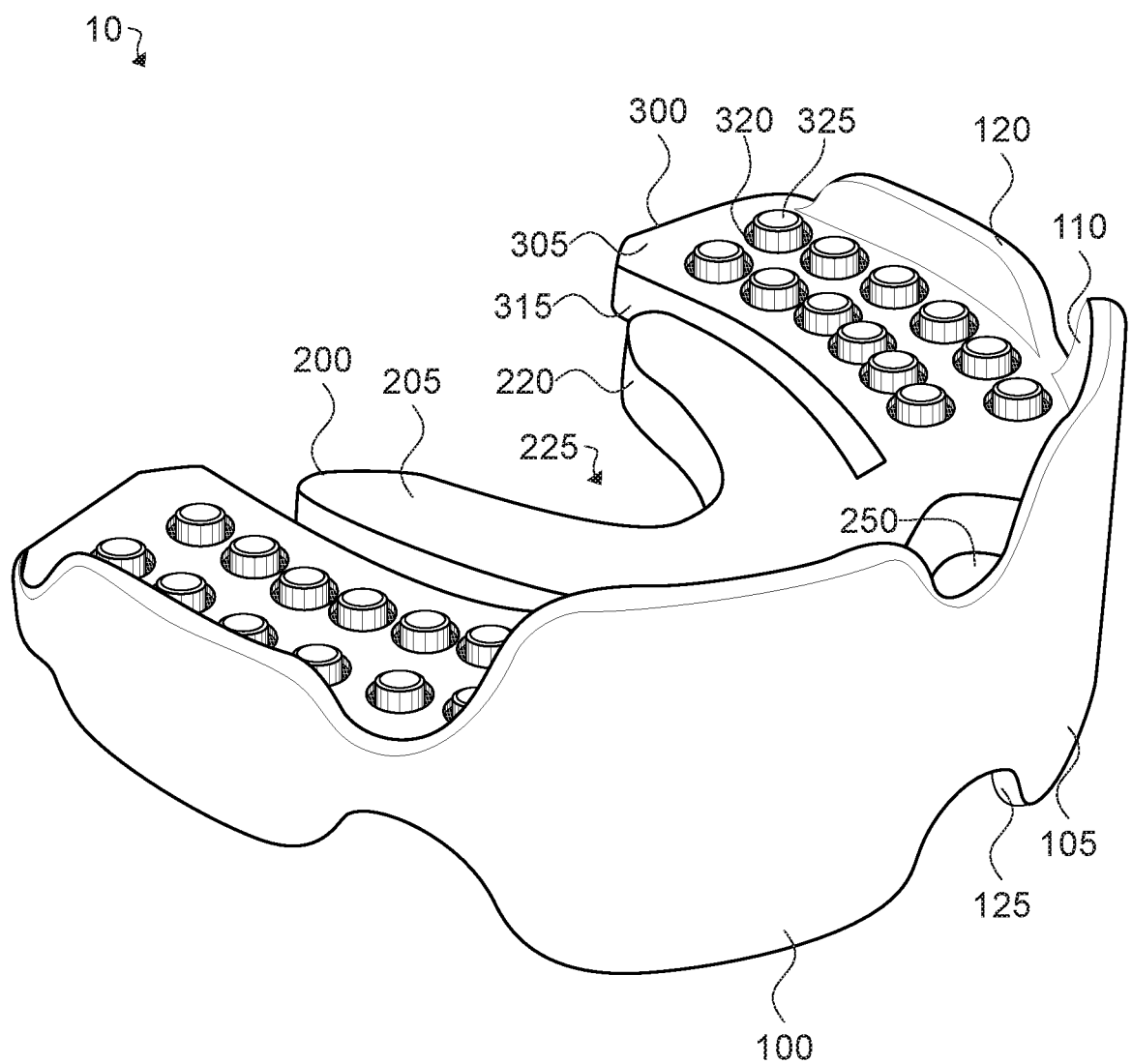
FIG. 8 shows an oblique, perspective view of the airflow inhibitor apparatus viewed from the front left top.

FIG. 2, FIG. 3, and FIG. 8 show a plurality of indentations 320. The plurality of indentations 320 may be formed in the pad upper surface 305 and/or in the pad lower surface 310. The indentations 320 may include a protrusion 325 as shown in these drawings, that extends away from the given indentation. The combination of indentations and protrusions allow the protrusions to flex laterally and provide improved comfort.

In an alternative embodiment, the indentations are tooth shaped. In this embodiment, the airflow inhibitor apparatus 10 is custom-made to fit the dental pattern of an individual. For example, a dental mold of the individual is made, and the airflow inhibitor apparatus 10 is created with indentations that specifically match the impression in the mold.

Returning to FIG. 2, a hole 250 is shown. The hole 250 extends through the pad wall 315 or through the shelf wall 215, depending on the arrangement. The hole 250 may be centered horizontally on the airflow inhibitor body 100. The hole 250 may improve the ability of the tongue shelf 200 to flex in the upward direction or the downward direction and may be helpful to comfortably accommodate therein, in the hole, the front teeth of the human mouth.

Returning to FIG. 3, note the support walls 330. The pad lower surface 310 is shown with support walls extending in the downward direction 31. Additional support walls may be provided elsewhere to help add stability to the apparatus. In one embodiment, the support walls may serve as guides that keep the tongue shelf, when depressed by the tongue of the wearer, centrally aligned.

Figure 6:
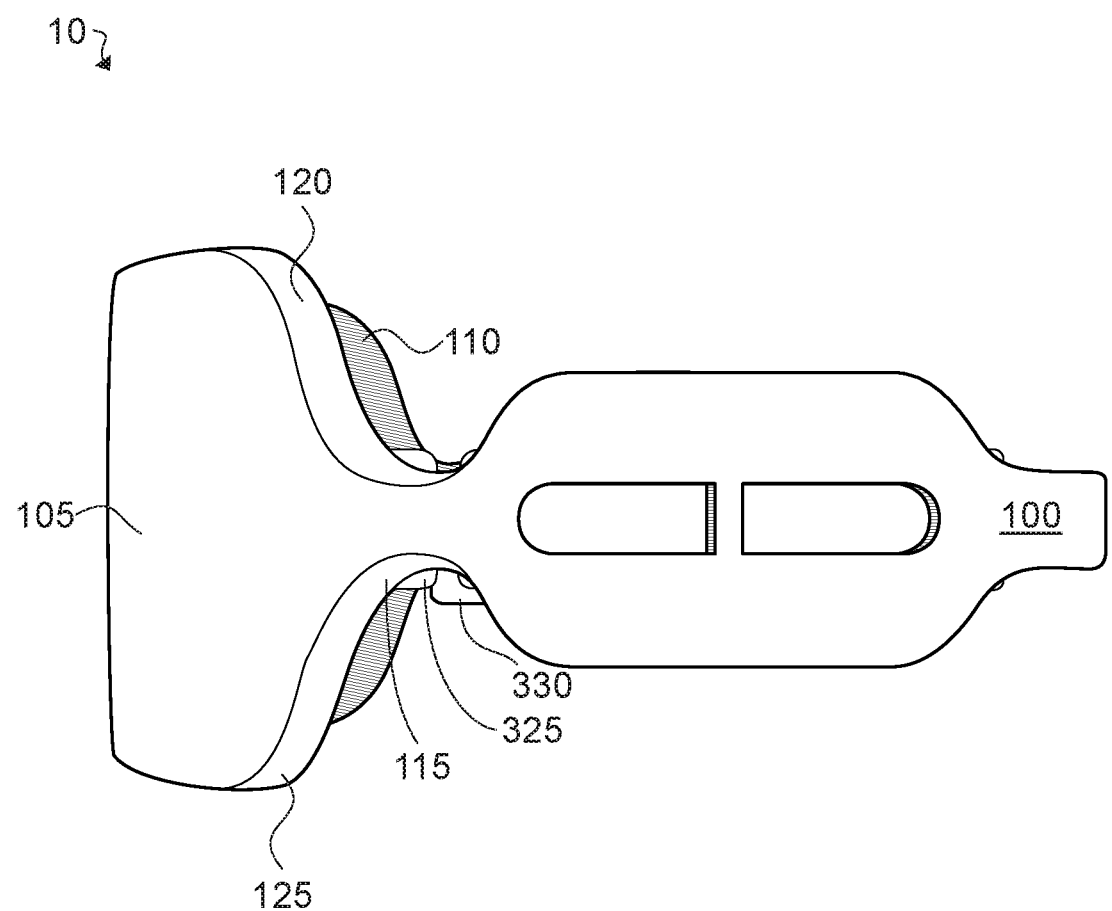
FIG. 6 shows the airflow inhibitor apparatus viewed from the right.
Figure 7:
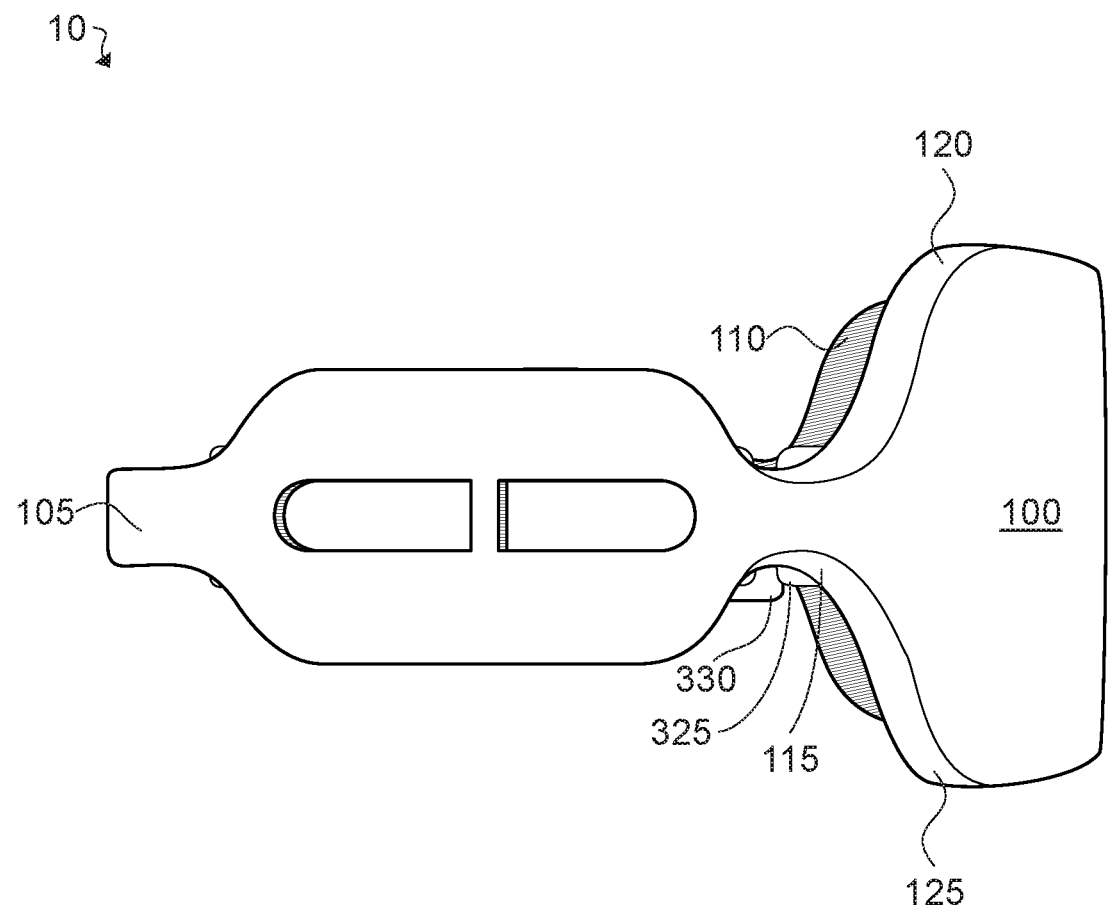
FIG. 7 shows the airflow inhibitor apparatus viewed from the left.

FIG. 6 and FIG. 7 show side views of the airflow inhibitor apparatus 10. In these views a decorative pattern appears on the cheek pads. The cheek pads, which may be shaped to suit the anatomy of the mouth and may take on shapes other than those depicted. The cheek pads may also include a decorative pattern such as that shown.

FIG. 8, in contrast to FIG. 1, includes the indentations 320, the protrusions 325, and the hole 250. In both drawing figures, the airflow inhibitor body 100 is integral with the tongue shelf 200 and the pad 300. In an alternative example, one or both of the tongue shelf 200 and the pad 300 are removable from the airflow inhibitor body 100 and may be replaced with a tongue shelf 200 or a pad 300 of a different size, thickness, or composition.

Figure 9:
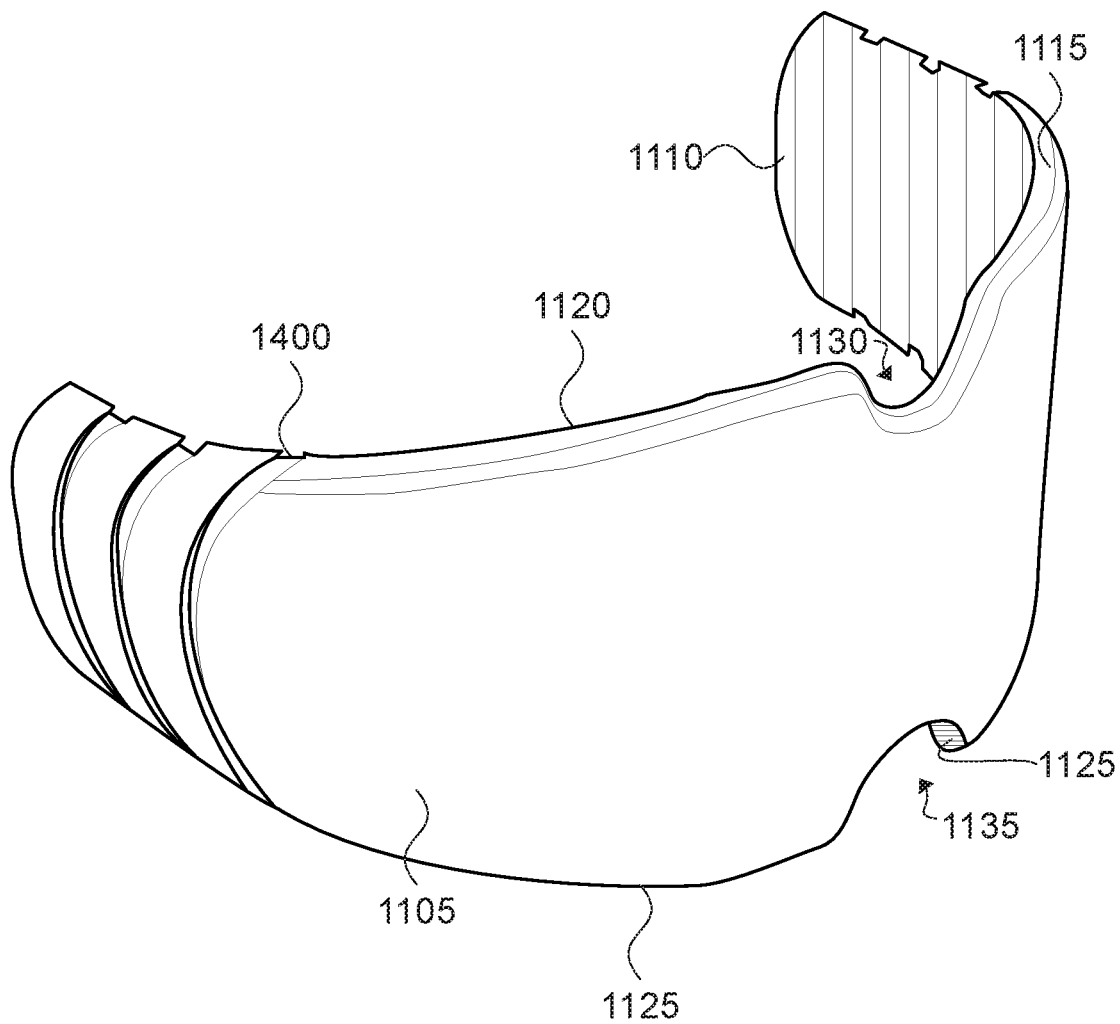
FIG. 9 shows an oblique, perspective view of another airflow inhibitor apparatus viewed from the front left top.

FIG. 9 shows an alternative version, referred to below as airflow inhibitor apparatus 20. The airflow inhibitor apparatus 20 has an airflow inhibitor body 1100 adapted to be disposed entirely between the teeth and lips, similar to the airflow inhibitor body 100 of the airflow inhibitor apparatus 10. Similar features are numbered similarly, except they are prepended with the numeral "1." FIG. 9 shows the body outer surface 1105, the body inner surface 1110, the body wall 1115, the body upper edge 1120, the body lower edge 1125, the first recess 1130, the second recess 1135.

In FIG. 9, the cheek pads are easily trimmed. The airflow inhibitor body 1100 is provided with thinned wall channels 1400 where the thickness of the body wall 1115 is thinner than in other parts. The thinned wall channels 1400 make it easier for a user to cut off part of the airflow inhibitor body 1100 by making such a cut along the thinned wall channels 1400. The thinned wall channels 1400 are curved so that, after the trimming operation, the resulting shape is curved, improving the comfort of the wearer.

Figure 10:
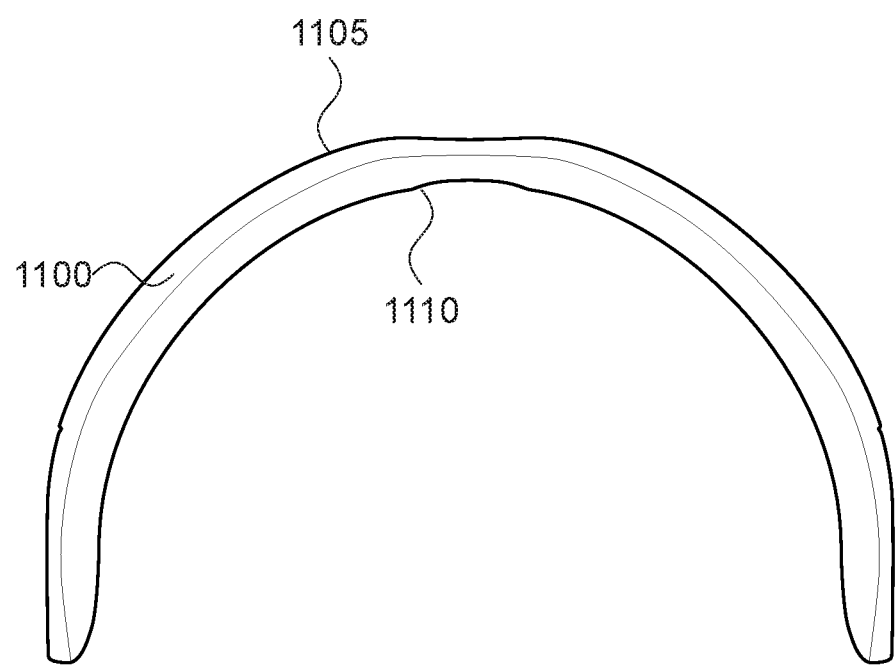
FIG. 10 shows the airflow inhibitor apparatus viewed from the top or bottom.

FIG. 10 shows the alternative version of FIG. 9, but without the thinned wall channels 1400.

Figure 11:
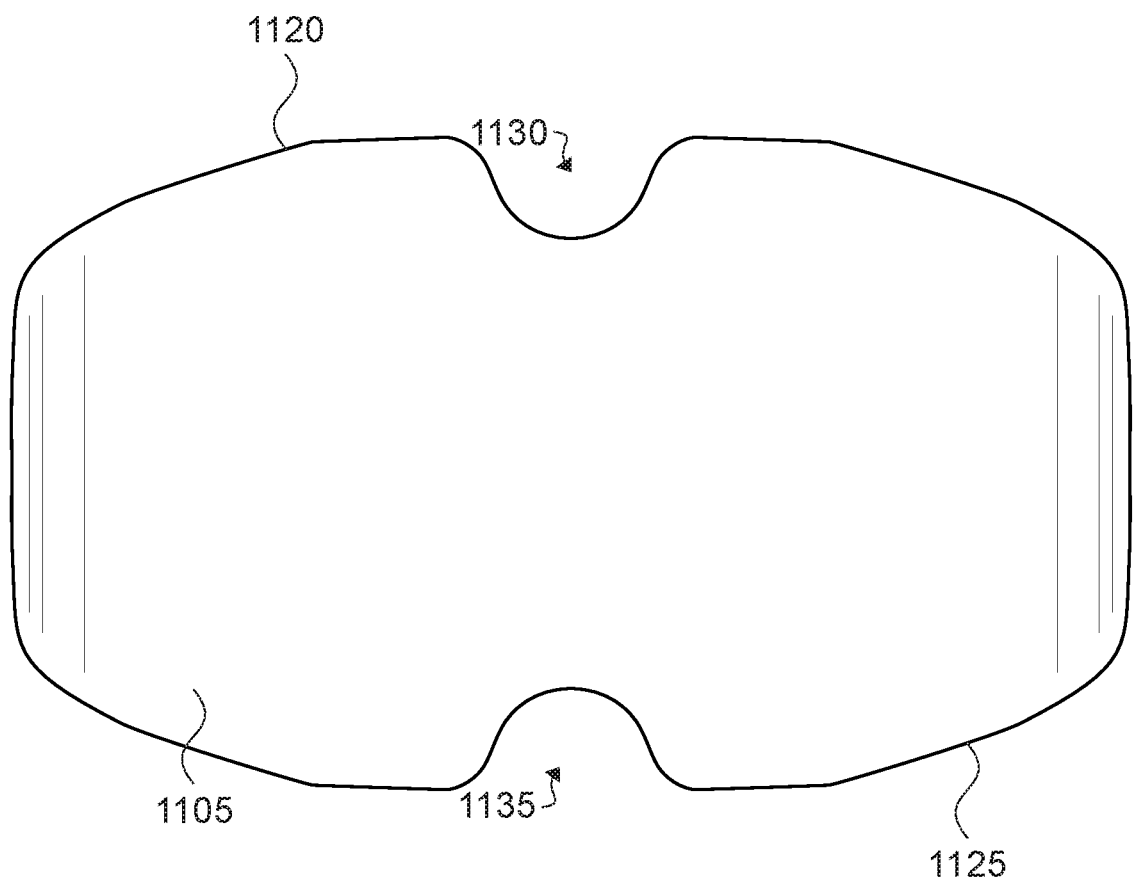
FIG. 11 shows the airflow inhibitor apparatus viewed from the front.

FIG. 11 illustrates the front view of the airflow inhibitor body 1100.

Figure 12:
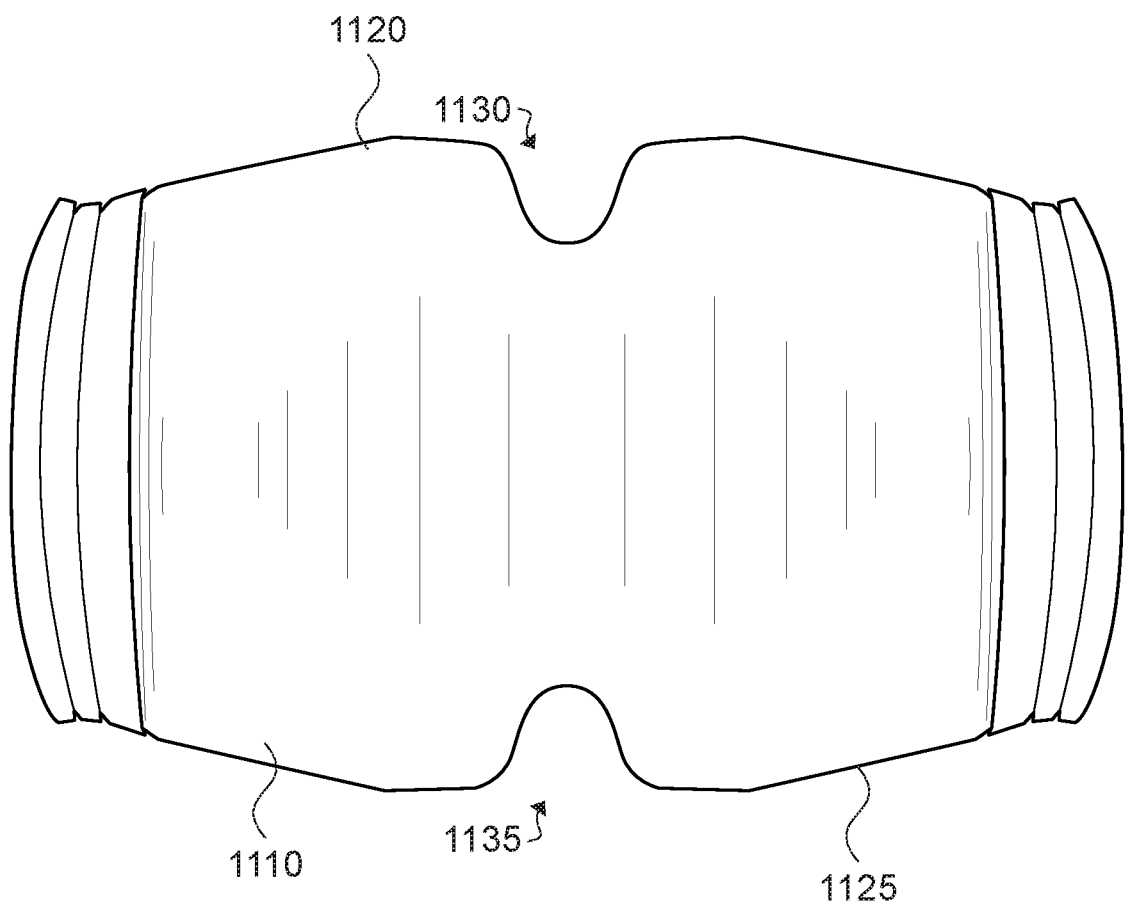
FIG. 12 shows the airflow inhibitor apparatus viewed from the rear.

FIG. 12 illustrates the view of the airflow inhibitor body 1100 from the rearward direction.

Figure 13:
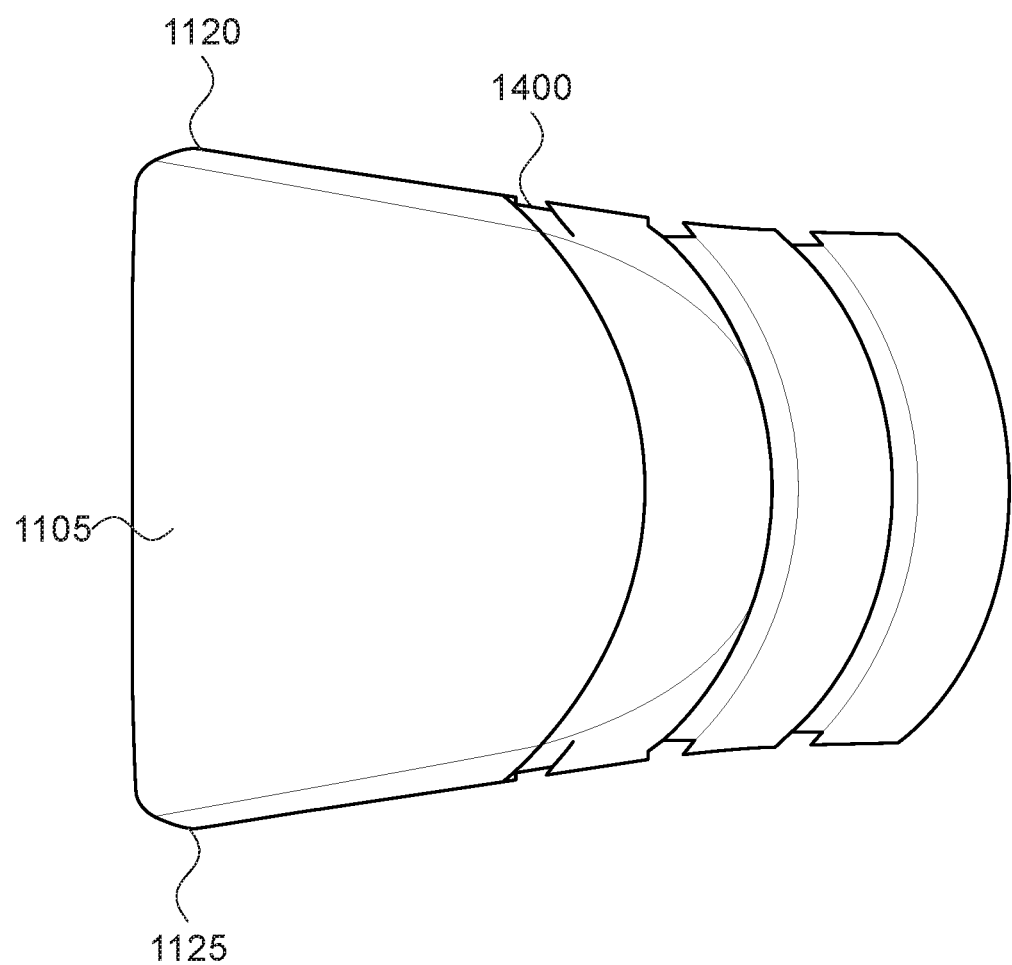
FIG. 13 shows the airflow inhibitor apparatus viewed from the right.
Figure 14:
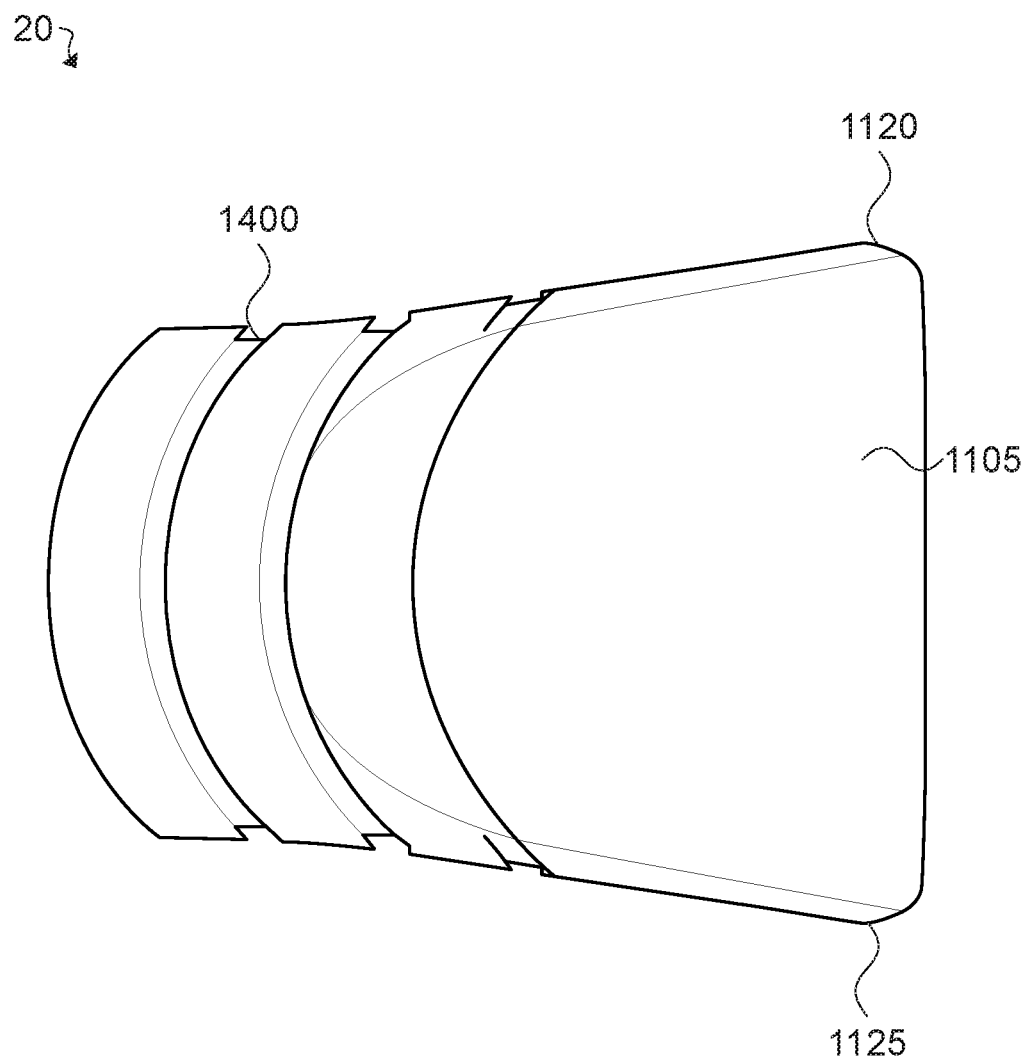
FIG. 14 shows the airflow inhibitor apparatus viewed from the left.

The thinned wall channels 1400 are depicted in the views from the left and from the right in FIG. 13 and FIG. 14.

The airflow inhibitor apparatus is designed to be worn in the mouth to train and promote nasal breathing by restricting, inhibiting, or preventing mouth breathing. The airflow inhibitor body helps to block the air flow through the mouth. It comprises a structure designed to be comfortably placed in between the teeth and the lips. It comprises a flat design curved to meet the shape of the mouth about the curvature of the teeth. The cutouts, or recesses, are positioned to accommodate the anatomy of the mouth.

The airflow inhibitor body can comprise different sections of different widths to more ergonomically fit inside the mouth. The side sections of the piece body may have cheek pads that are smaller in width than the front of the airflow inhibitor body. In alternative embodiments, the airflow inhibitor body may accommodate other dental accessories including, but not limited to, dental braces.

Many other possible modifications and variations can be made without departing from the spirit and scope of the invention.

The invention claimed is:

1. An airflow inhibitor apparatus, intended for use in a human mouth having lips, teeth, an upper jaw, a lower jaw, and a tongue, the teeth including front teeth, the airflow inhibitor apparatus comprising:
an airflow inhibitor body, adapted to be disposed in the human mouth between the lips and the teeth;
the airflow inhibitor body having a body outer surface and a body inner surface, the body outer surface being adjacent to the lips and the body inner surface being adjacent to the teeth when disposed in the human mouth;
the airflow inhibitor body having a body wall between the body outer surface and the body inner surface;
the body wall having a body upper edge and a body lower edge, the body upper edge being nearer to the upper jaw and the body lower edge being nearer to the lower jaw when disposed in the human mouth;
the airflow inhibitor body having a first recess centrally disposed along the body upper edge;
the airflow inhibitor body having a second recess centrally disposed along the body lower edge;
a bite pad that extends laterally from the body inner surface, has a pad upper surface and a pad lower surface, and has a pad wall between the pad upper surface and the pad lower surface, the bite pad extending from the body inner surface to a position adapted to be between the teeth when disposed in the human mouth;
a tongue shelf attached to the bite pad;
the tongue shelf extending laterally from the bite pad and centered upon the body inner surface;
the tongue shelf having a shelf upper surface and a shelf lower surface, the shelf upper surface being nearer the upper jaw and the shelf lower surface being nearer the lower jaw when disposed in the human mouth;
the tongue shelf having a shelf wall between the shelf upper surface and the shelf lower surface;
the tongue shelf having a shelf rearward edge, the shelf rearward edge being nearer to the tongue than to the teeth when disposed in the human mouth;
the tongue shelf having a shelf forward edge spaced from the body inner surface by a hole in the bite pad;
the tongue shelf having a tongue recess centrally disposed along the shelf rearward edge; and
the hole being shaped to accommodate therein the front teeth of the human mouth.

2. The airflow inhibitor apparatus of claim 1, further comprising indentations that are formed in one or more of the pad upper surface and the pad lower surface.

3. The airflow inhibitor apparatus of claim 2, wherein the indentations are shaped to accommodate the teeth.

4. The airflow inhibitor apparatus of claim 2, further comprising protrusions that extend outward from within the indentations.

5. The airflow inhibitor apparatus of claim 2, further comprising one or more support walls extending perpendicularly from the pad lower surface.

6. The airflow inhibitor apparatus of claim 2, wherein the airflow inhibitor body is integral with the tongue shelf and the bite pad.

7. An airflow inhibitor apparatus, comprising:
an airflow inhibitor body, the airflow inhibitor body being an arcuate, being curved symmetrically about a first axis, extending horizontally along a second axis, and extending depthwise along a third axis;
the airflow inhibitor body having:
a body outer surface that is convex and a body inner surface that is concave, the body outer surface defining a forward direction of the third axis and the body inner surface defining a rearward direction of the third axis;
a body wall between the body outer surface and the body inner surface, the body wall having a body upper edge in an upward direction of the first axis and a body lower edge in a downward direction of the first axis;
a line of symmetry along a plane that contains the first axis and the third axis;
a first recess disposed along the line of symmetry along the body upper edge; and
a second recess disposed along the line of symmetry along the body lower edge;
a bite pad extending from the body inner surface in the rearward direction of the third axis, having a pad upper surface and a pad lower surface, and having a pad wall between the pad upper surface and the pad lower surface a tongue shelf, attached to the bite pad and extending in the rearward direction of the third axis, the tongue shelf having:
- a shelf upper surface in the upward direction of the first axis and a shelf lower surface in the downward direction of the first axis;
- a shelf wall between the shelf upper surface and the shelf lower surface;
- a shelf rearward edge in the rearward direction of the third axis;
- a shelf forward edge separated from the body inner surface by a hole in the bite pad, the hole having a dimension, along the second axis, adapted to accommodate front teeth of a human mouth; and
- a tongue recess along the shelf rearward edge.

8. The airflow inhibitor apparatus of claim 7, wherein one or more of the pad upper surface and the pad lower surface have a plurality of indentations.

9. The airflow inhibitor apparatus of claim 8, wherein at least one of the plurality of indentations is shaped to accommodate a tooth.

10. The airflow inhibitor apparatus of claim 8, further comprising, within at least one of the plurality of indentations, a protrusion that extends away from the at least one of the plurality of indentations.

11. The airflow inhibitor apparatus of claim 7, further comprising one or more support walls extending, in the downward direction of the first axis, from the pad lower surface.

12. The airflow inhibitor apparatus of claim 7, wherein the airflow inhibitor body is integral with the bite pad and the bite pad is integral with the tongue shelf.

* * * * *